(12) United States Patent
Xiang et al.

(10) Patent No.: US 12,226,656 B2
(45) Date of Patent: Feb. 18, 2025

(54) ORTHOGONAL DOUBLE-LAYER GRATING DYNAMIC INTENSITY MODULATION SEGMENTATION METHOD BASED ON QUADRANT

(71) Applicant: SUZHOU LINATECH MEDICAL SCIENCE AND TECHNOLOGY CO., LTD., Suzhou (CN)

(72) Inventors: Yunfei Xiang, Suzhou (CN); Huer Wen, Suzhou (CN); Jonathan Yi Yao, Suzhou (CN)

(73) Assignee: SUZHOU LINATECH MEDICAL SCIENCE AND TECHNOLOGY CO., LTD., Suzhou (CN)

( * ) Notice: Subject to any disclaimer, the term of this patent is extended or adjusted under 35 U.S.C. 154(b) by 216 days.

(21) Appl. No.: 17/915,385

(22) PCT Filed: Nov. 20, 2020

(86) PCT No.: PCT/CN2020/130429
§ 371 (c)(1),
(2) Date: Sep. 28, 2022

(87) PCT Pub. No.: WO2021/248837
PCT Pub. Date: Dec. 16, 2021

(65) Prior Publication Data
US 2023/0132237 A1   Apr. 27, 2023

(30) Foreign Application Priority Data
Jun. 8, 2020   (CN) .......................... 202010515666.6

(51) Int. Cl.
*A61N 5/10*   (2006.01)

(52) U.S. Cl.
CPC ........... *A61N 5/1036* (2013.01); *A61N 5/103* (2013.01); *A61N 5/1031* (2013.01); *A61N 5/1045* (2013.01); *A61N 5/1047* (2013.01)

(58) Field of Classification Search
CPC ........ A61N 5/10; A61N 5/103; A61N 5/1031; A61N 2005/1034; A61N 5/1036;
(Continued)

(56) References Cited

U.S. PATENT DOCUMENTS 5,591,983 A * 1/1997 Yao ...................... A61N 5/1045
378/152
6,266,393 B1* 7/2001 Ein-Gal ............... A61N 5/1042
378/152
(Continued)

FOREIGN PATENT DOCUMENTS

CN   107823806 A   3/2018
CN   108175953 A   6/2018
(Continued)

*Primary Examiner* — Allen C. Ho
(74) *Attorney, Agent, or Firm* — MUNCY, GEISSLER, OLDS & LOWE, P.C.

(57) ABSTRACT

The invention discloses an orthogonal dual-layer grating dynamic intensity modulation segmentation method based on quadrant, specifically include the following steps: S1: the fluence distribution under each beam is calculated through the radiation treatment planning system; S2: use orthogonal double-layer collimator for fluence segmentation; S3: divide the quadrant, divide the field surrounded by the upper, lower, left and right leaves into at least two quadrants, to obtain the fluence distribution and the corresponding leaf sequence of each quadrant; S4: perform regional planning of the fluence in each quadrant to obtain multiple different regions and determine the segmentation mode of different regions; S5: for any quadrant, use two mutually orthogonal leaf groups for segmentation. The present invention completes the dynamic segmentation of any shape target area and multiple
(Continued)

target areas through the mutual cooperative movement of the upper and lower layers of orthogonal leaves, realizes the dynamic segmentation of the upper and lower layers of the orthogonal dual-layer collimator from two directions, avoids the end surface perspective between the leaves, and improves the segmentation efficiency.

10 Claims, 9 Drawing Sheets

(58) Field of Classification Search
CPC .. A61N 5/1037; A61N 5/1042; A61N 5/1045; A61N 5/1047; A61N 5/1048; A61N 5/1049
USPC .......................................... 378/65, 150–152
See application file for complete search history.

(56) References Cited

U.S. PATENT DOCUMENTS

| | | | | |
|---|---|---|---|---|
| 6,473,490 B1* | 10/2002 | Siochi | .................... | A61N 5/103 378/65 |
| 6,526,123 B2* | 2/2003 | Ein-Gal | ................ | A61N 5/1042 378/65 |
| 6,577,707 B2* | 6/2003 | Siochi | .................. | A61N 5/1042 378/65 |
| 6,600,810 B1* | 7/2003 | Hughes | ................ | A61N 5/1045 378/152 |
| 6,647,092 B2* | 11/2003 | Eberhard | ................ | G21K 1/04 378/65 |
| 6,661,871 B2* | 12/2003 | Siochi | .................. | A61N 5/1042 378/65 |
| 6,757,355 B1* | 6/2004 | Siochi | .................. | A61N 5/1042 378/65 |
| 6,853,705 B2* | 2/2005 | Chang | .................. | A61N 5/1042 378/65 |
| 6,999,556 B2* | 2/2006 | Nakano | .................. | A61N 5/103 378/65 |
| 7,085,348 B2* | 8/2006 | Kamath | ................ | A61N 5/103 378/65 |
| 7,283,611 B1* | 10/2007 | Luan | ...................... | A61N 5/103 378/65 |
| 7,573,978 B2* | 8/2009 | Kamath | .................. | G21K 1/04 378/65 |
| 7,796,731 B2* | 9/2010 | Nord | .................... | A61N 5/1042 378/65 |
| 8,009,794 B2* | 8/2011 | Partain | .................. | G21K 1/043 378/7 |
| 8,014,494 B2* | 9/2011 | Yu | ........................ | A61N 5/1047 378/65 |
| 8,615,068 B2* | 12/2013 | Gunawardena | ...... | A61N 5/1036 378/65 |
| 10,398,911 B2* | 9/2019 | Nord | .................... | A61N 5/1045 |
| 10,420,958 B2* | 9/2019 | Kauppinen | .......... | A61N 5/1036 |
| 10,441,814 B2* | 10/2019 | Nord | .................... | A61N 5/1036 |
| 10,449,389 B2* | 10/2019 | Ollila | .................... | A61N 5/1045 |
| 10,500,417 B2* | 12/2019 | Kuusela | ............... | A61N 5/1045 |
| 10,510,456 B2* | 12/2019 | Zhang | .................... | G21K 1/04 |
| 10,751,550 B2* | 8/2020 | Schnarr | ................ | A61N 5/1045 |
| 10,770,196 B2* | 9/2020 | Schnarr | ................ | A61N 5/1047 |
| 10,960,229 B2* | 3/2021 | Ni | ........................ | G01R 33/3403 |
| 10,987,523 B2* | 4/2021 | Sheng | .................. | A61N 5/1036 |
| 11,000,706 B2* | 5/2021 | Kawrykow | .......... | A61N 5/1049 |
| 11,147,985 B2* | 10/2021 | Isola | .................... | A61N 5/1031 |
| 11,344,749 B2* | 5/2022 | Landrith | .............. | A61N 5/1075 |
| 11,446,518 B2* | 9/2022 | Li | ........................ | A61N 5/1045 |
| 11,511,130 B2* | 11/2022 | Stahl | .................... | A61N 5/1042 |
| 11,633,625 B2* | 4/2023 | Wang | .................... | A61B 5/055 324/307 |
| 11,679,278 B2* | 6/2023 | Miettinen | ................ | A61B 6/06 600/427 |
| 11,692,851 B2* | 7/2023 | Iskandar | .............. | A61N 5/1075 324/207.21 |
| 11,697,030 B2* | 7/2023 | Schnarr | ................ | A61N 5/1045 378/65 |
| 11,730,977 B2* | 8/2023 | Stahl | .................... | A61N 5/1036 600/1 |
| 11,759,655 B2* | 9/2023 | Nord | .................... | G21K 1/046 250/505.1 |
| 11,986,675 B2* | 5/2024 | Wösle | .................. | A61N 5/1047 |
| 12,029,919 B2* | 7/2024 | Wen | .................... | A61N 5/1031 |
| 2006/0045238 A1 | 3/2006 | Nguyen | | |

FOREIGN PATENT DOCUMENTS

| | | |
|---|---|---|
| CN | 109499011 A | 3/2019 |
| CN | 110170109 A | 8/2019 |
| CN | 110215623 A | 9/2019 |
| CN | 110404185 A | 11/2019 |
| CN | 111681736 A | 9/2020 |

* cited by examiner

ORTHOGONAL DOUBLE-LAYER GRATING DYNAMIC INTENSITY MODULATION SEGMENTATION METHOD BASED ON QUADRANT

TECHNICAL FIELD

The present invention relates to a method of multi-leaf grating specifically relates to an orthogonal dual-layer grating dynamic intensity modulation segmentation method based on quadrant.

BACKGROUND

In order to protect healthy tissue from radiation therapy for tumor (target area), multi-leaf collimator (MLC) is generally used to adjust the range and intensity of radiation irradiation, intensity modulated radiotherapy (IMRT).

MLC was initially applied to classical conformal radiotherapy, replacing the block in conventional radiotherapy, forming the desired irradiation field shape. The MLC consists of two groups of closely arranged leaves. Each leaves is made of tungsten alloy in a long strip and driven by a small motor. Compared with the field block, MLC has significant advantages: shorter treatment time, shorter time interval between simulation positioning and treatment, greatly improving the efficiency of radiation therapy; better attenuation of radiation than block; easy to operate without moving bulky blocks; reusable; no harmful gas or dust; flexibility to respond to target changes and correct errors.

Orthogonal dual-layer collimator contains two layers of MLC lying perpendicular to each other, the consistency of the MLC shape and the target area boundary can be achieved by the corresponding leaves at the edge position of the target area, and the conformity of the beam field and the target area can be improved. Since there are at least two layers of collimators are perpendicular to each other, it can adjust the same shape of the window as required, block the leakage rays between the leaves by two layer collimators, greatly reduce the ray leakage, and effectively reduce the penumbra area, thus, the treatment can be accurately positioned, which providing conditions for less fraction treatment and high-dose treatment. Moreover, the superimposed leaves make the collimator rays penetrating the leave decay to a safe range, which improves the use efficiency of the equipment and reduces the medical cost and the burden on patients. At the same time, since the upper leaves and lower leaves are perpendicular to each other, they can move in two directions vertical to each other.

At present, the algorithm of MLC dynamic segmentation is mainly the dynamic sliding window scanning segmentation technology of Sliding window, but due to the gap between a pair of opposite leaves during the scanning process, the low dose segmentation of concave target area and internal target ring target area cannot be completed. G. Grigorow in the literature SU-GG-T-93: Dosimetry Evaluation and Correction of DMLC Control Points for Sliding Window IMRT proposed a method to change the dose rate and adjust the maximum leaves speed to reduce the leakage between leaves, However, the problem of the leakage between the leaves cannot be fundamentally eliminated. The method for simultaneous dynamic segmentation of orthogonal double layer collimators has not been mentioned, how to solve the problem of concave and annular target areas, and how to use orthogonal double-layer collimators to track lung dynamic target areas still need to inject new solutions.

Existing algorithms for MLC dynamic segmentation mainly have the following problems:

First, the projection width of the leaves of the single-layer MLC in the isocenter plane is usually between 0.5 cm~1.0 cm, and the irradiation fields formed by the single-layer MLC have step boundaries, which cannot be exactly consistent with the expected boundary-smooth target area boundary. Although the conformity of the field can be improved by making the leaf width of the MLC thinner and thinner, it cannot be theoretically infinitely thin due to the leaf width is machined, so the serrated field edge cannot be completely eliminate.

Second, because in the range of intensity beam, there are more pairs of closed leaves, but because of mechanical and motion collision considerations, there is a gap between paired closed leaves, there is about 20%-30% of the leaves end surface transmission;

Third, a single layer of MLC cannot complete the lung dynamic target area tracking therapy from two directions.

SUMMARY

To solve the above technical problems, the present invention proposes an orthogonal dual-layer grating dynamic intensity modulation segmentation method based on quadrant.

To achieve the above purpose, the technical scheme of the present invention is as follows:

An orthogonal dual-layer grating dynamic intensity modulation segmentation method based on quadrant, comprising the following steps:
- S1: the fluence distribution under each radiation field is calculated by the treatment planning system, it can be expressed as a fluence $F(x,y)$ within the radiation field range in the isocenter plane;
- S2: use orthogonal double-layer collimator for fluence segmentation;
- S3: divide the quadrant, divide the field surrounded by the upper, lower, left and right leaves into at least two quadrants, to obtain the fluence distribution and the corresponding leaf sequence of each quadrant;
- S4: perform regional planning of the fluence in each quadrant to obtain multiple different regions and determine the segmentation mode of different regions;
- S5: for any quadrant, use two mutually orthogonal leaf groups for segmentation.

On the basis of the above technical scheme, the following improvements can also be made:

As a preferred scheme, step S2 includes that rays are projected under the isocenter plane coordinate system S-XY, and the upper and lower leaves are located at four directions of the isocenter plane respectively.

As a preferred scheme, for step S3, the maximum point or minimum point in the target area can be a segmentation center.

As a preferred scheme, for step S3, if there is a concave fluence distribution or an annular target area fluence distribution, the quadrant division takes the minimum point as the segmentation center;

if there are multiple concave areas, the center of the concave target area is located on the intersection line of the two quadrants.

As a preferred scheme, for step S3, after completing the quadrant segmentation, each quadrant corresponds to a ray fluence within one region of the beam range, and corresponds to at least one pair of mutually orthogonal leaf groups.

As a preferred scheme, step S4 specifically includes the following: the surroundings of any peak or trough in the fluence can be divided into four regions A1, A2, A3, A3 and A4 according to the value of partial derivatives;

when $\partial F/\partial x <= 0$, and $\partial F/\partial y <= 0$, the region is region A1;
when $\partial F/\partial x > 0$, and $\partial F/\partial y <= 0$, the region is region A2;
when $\partial F/\partial x <= 0$, and $\partial F/\partial y > 0$, the region is region A3;
when $\partial F/\partial x > 0$, and $\partial F/\partial y > 0$, the region is region A4.

As a preferred scheme, step S5 specifically comprises the following steps:

S5.1: determine the initial position of the leaves;
S5.2: establish the leaves movement trajectory function;
S5.3: apply the time-delay differential equation to solve the leaf motion trajectory function.

As a preferred solution, step S5.1 specifically includes the following: two orthogonal leaf groups, defining one group as an active leaf, the other group as a passive leaf, the active leaf moving from the beam edge to the beam center, and the passive leaf retreating from the beam center to the beam edge;

the initial position can be determined as the active leaf at the edge of the field and the passive leaf at the quadrant junction.

As a preferred solution, step S5.2 specifically comprises the following: under the premise of a given accelerator dose rate and the blade moving in one direction, a leaf trajectory is described by a corresponding relationship between leaf position and fluence size, given the accelerator dose rate and the leaves moving along one direction;

the leaf end position is used as the leaf position, the relationship between the leaf position and its corresponding fluence size is a monotonic function in the absence of other leaves blocking.

As a preferred scheme, step S5.3 specifically comprises the following: knowing the starting position of each leaf position, the fluence function of the next moment by the fluence function of the previous position.

The present invention completes the dynamic segmentation of any shape target area (concave target area, annular target area, etc.) and multiple target areas through the mutual cooperative movement of the upper and lower layers of orthogonal leaves, realizes the dynamic segmentation of the upper and lower layers of the orthogonal dual-layer collimator from two directions, avoids the end surface perspective between the leaves, and improves the segmentation efficiency.

BRIEF DESCRIPTION OF THE DRAWINGS

FIG. 2($a$) and FIG. 2($b$) show the position distribution of orthogonal dual-layer collimator under the beam frame system provided by the invention embodiment;

FIG. 2($a$) is a schematic diagram of the structure of the rays and the dual-layer collimator;

FIG. 2($b$) shows the position relationship between the upper leaves, the lower leaves and the isocenter plane.

FIG. 4($a$), FIG. 4($b$), and FIG. 4($c$) show a diagram of three typical quadrant segmentation modes provided by the invention embodiment;

FIG. 4($a$) is a diagram of the first quadrant segmentation mode;

FIG. 4($b$) is a diagram of the second quadrant segmentation mode;

FIG. 4($c$) is a diagram of the third quadrant segmentation mode;

FIG. 13($a$) and FIG. 13($b$) show a motion track curve of an active leaf or a passive leaf in the first quadrant provided by the invention embodiment;

FIG. 13($a$) is the motion trajectory diagram of the right leaves;

FIG. 13($b$) is the motion trajectory diagram of the front leaves.

Among them: 1—peak or trough; 2—valley center.

DETAILED DESCRIPTION OF THE EMBODIMENTS

The preferred embodiments of the present invention are described in detail below in connection with the accompanying drawings.

To achieve the object of the present invention, in some embodiments of an orthogonal dual-layer grating dynamic intensity modulation segmentation method based on quadrant, an orthogonal dual-layer grating dynamic intensity modulation segmentation method based on quadrant, comprising the following steps of:

S1: the fluence distribution under each radiation field is calculated by the treatment planning system, it can be expressed as a fluence $F(x,y)$ within the radiation field range in the isocenter plane;

S2: use orthogonal double-layer collimator for fluence segmentation;

S3: divide the quadrant, divide the field surrounded by the upper, lower, left and right leaves into at least two quadrants, to obtain the fluence distribution and the corresponding leaf sequence of each quadrant;

S4: perform regional planning of the fluence in each quadrant to obtain multiple different regions and determine the segmentation mode of different regions;

S5: for any quadrant, use two mutually orthogonal leaf groups for segmentation.

Figure 3:
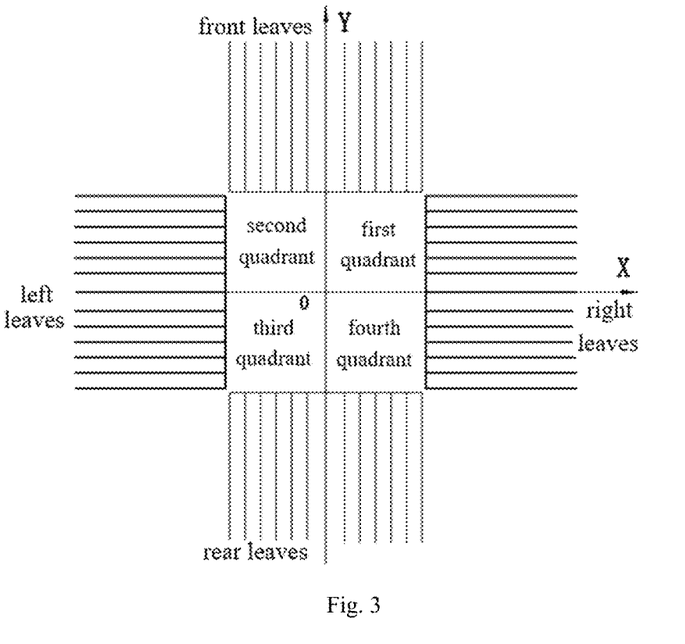
FIG. 3 is a schematic diagram of the quadrant division and the leaf sequence assignment of the fluence provided by the invention embodiment.

In step S3, as shown in FIG. 3, each quadrant corresponds to two different sets of leaf sequences, and the adjacent quadrant combination may also form a separate quadrant that may correspond to three different leaves; the quadrant division shall try to ensure the total time for each quadrant.

In order to further optimize the implementation effect of the present invention, in other embodiments, the other features are the same, except that the step S2 includes that rays are projected under the isocenter plane coordinate system S-XY, and the upper and lower leaves are located at four directions of the isocenter plane respectively.

In order to further optimize the implementation effect of the present invention, in other embodiments, the other feature techniques are the same, except in that for the step S3, the maximum point or minimum point in the target area can be a segmentation center.

Figure 4A:
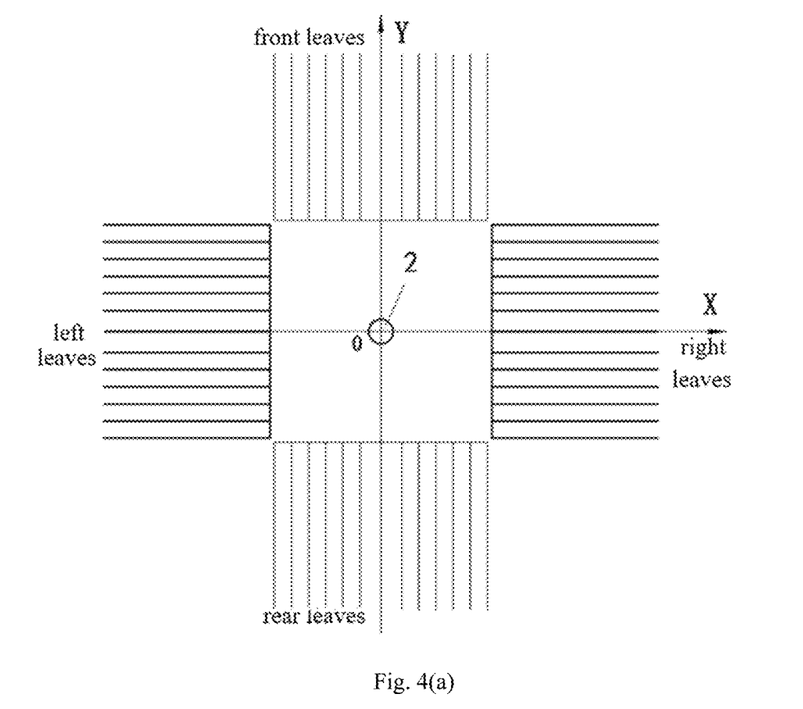
Figure 4B:
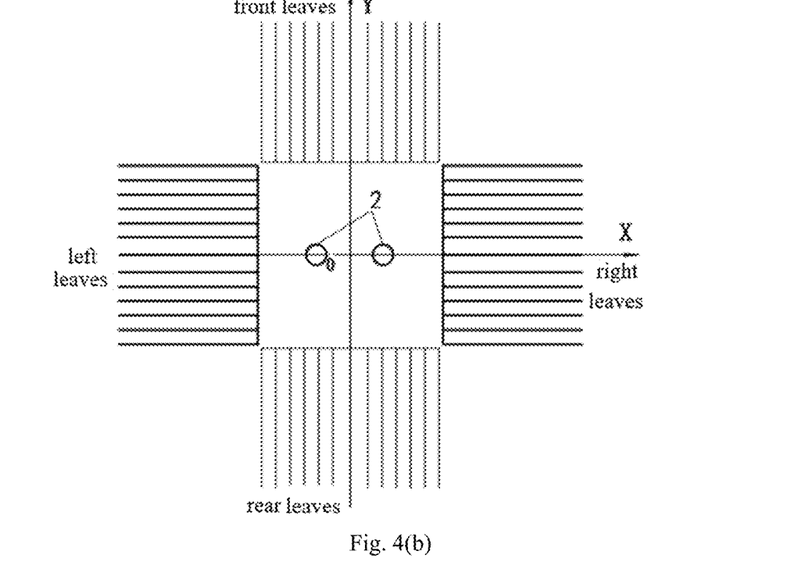
Figure 4C:
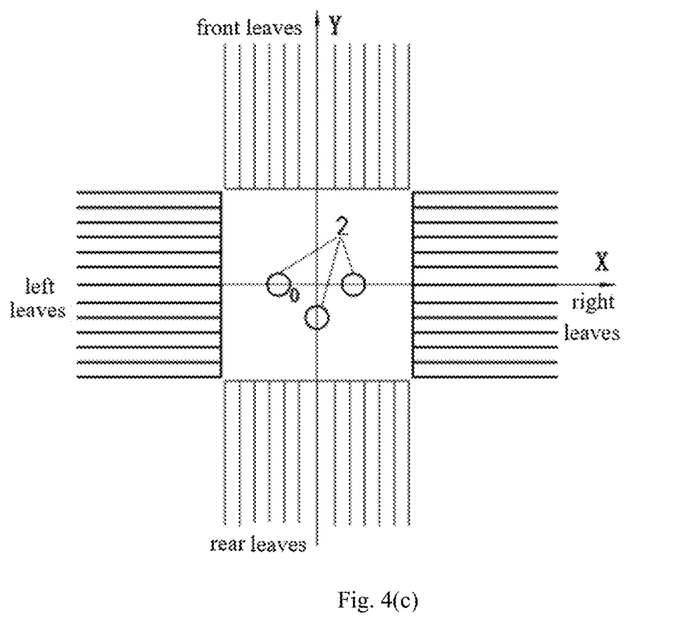

In order to further optimize the implementation effect of the present invention, in other embodiments, the other feature techniques are the same, as shown in FIG. 4, for step S3, if there is a concave fluence distribution or an annular target area fluence distribution, the quadrant division takes the minimum point as the segmentation center;
  if there are multiple concave areas, the center of the concave target area is located on the intersection line of the two quadrants.
  Specifically, the "○" in FIG. 4 represents the valley center 2.

In order to further optimize the implementation effect of the present invention, in other embodiments, the remaining features are the same, except in that, for step S3, after completing the quadrant segmentation, each quadrant corresponds to a ray fluence within one region of the beam range, and corresponds to at least one pair of mutually orthogonal leaf groups.

Figure 9:
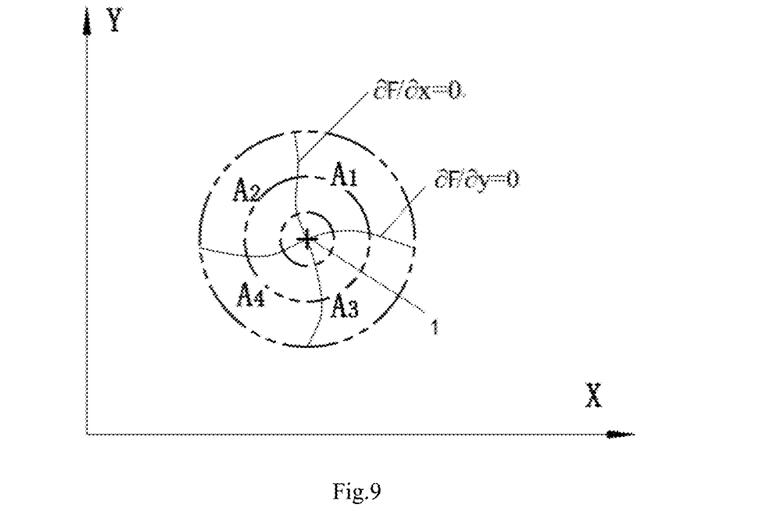
FIG. 9 is a schematic diagram of the area division around a peak or trough provided by the invention embodiment.

In order to further optimize the implementation effect of the present invention, in other embodiments, the other features are the same, in that step S4 specifically includes the following: as shown in FIG. 9, the surroundings of any peak or trough 1 in the fluence can be divided into four regions A1, A2, A3, A3 and A4 according to the value of partial derivatives;
  when $\partial F/\partial x \le 0$, and $\partial F/\partial y \le 0$, the region is region A1;
  when $\partial F/\partial x > 0$, and $\partial F/\partial y \le 0$, the region is region A2;
  when $\partial F/\partial x \le 0$, and $\partial F/\partial y > 0$, the region is region A3;
  when $\partial F/\partial x > 0$, and $\partial F/\partial y > 0$, the region is region A4.

Figure 10:
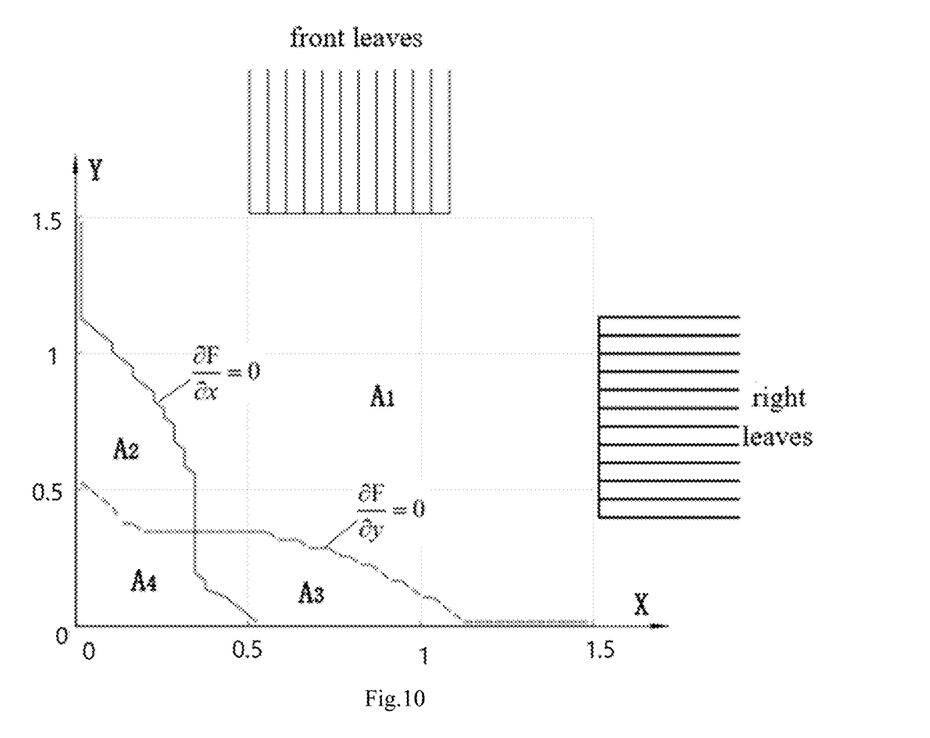
FIG. 10 is a schematic diagram of the area division within the first quadrant provided by the invention embodiment.

In this embodiment, in order to improve the segmentation efficiency, different regions are adopted for different regions in a quadrant. As shown in FIG. 10, in the first quadrant, regions A1 and A3 can be independently divided in right leaves, anterior leaves and A2 can be used for independent segmentation in region A1, and two groups of leaves are required for orthogonal coordination segmentation in region A4.

To further optimize the implementation effect of the present invention, in other embodiments, the remaining characteristic techniques are the same, except that step S5 specifically includes the following steps:
  S5.1: determine the initial position of the leaves;
  S5.2: establish the leaves movement trajectory function;
  S5.3: apply the time-delay differential equation to solve the leaf motion trajectory function.

Further, step S5.1 includes the following: two orthogonal leaf groups, defining one group as an active leaf, the other group as a passive leaf, the active leaf moving from the beam edge to the beam center, and the passive leaf retreating from the beam center to the beam edge;
  the initial position can be determined as the active leaf at the edge of the field and the passive leaf at the quadrant junction.

Figure 5:
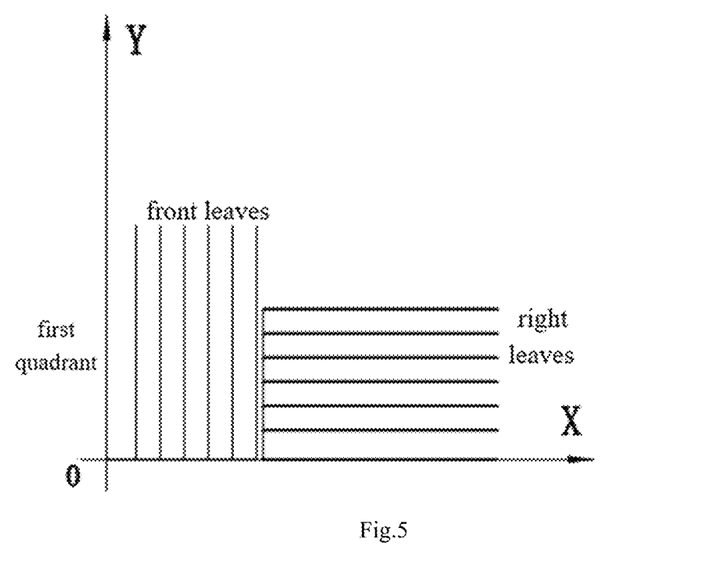
FIG. 5 is a schematic determination of the initial position of the active (passive) leaf of the first quadrant provided by the invention embodiment.

It is worth noting that it is necessary to avoid that a pair of oppositely arranged leaves are the passive leaf when defining the passive leaf. As shown in FIG. 5, it is an initial position situation of the first quadrant leaves, the right leaves is acted as a set of active leaf and the left leaves is acted as a set of passive leaf.

Figure 6:
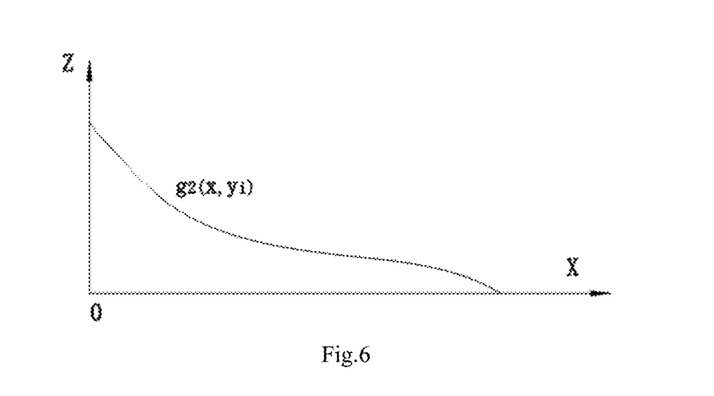
FIG. 6 is a graph showing the functional relationship between the position of the right leaves in the first quadrant and the size of the fluence value provided by the invention embodiment.
Figure 7:
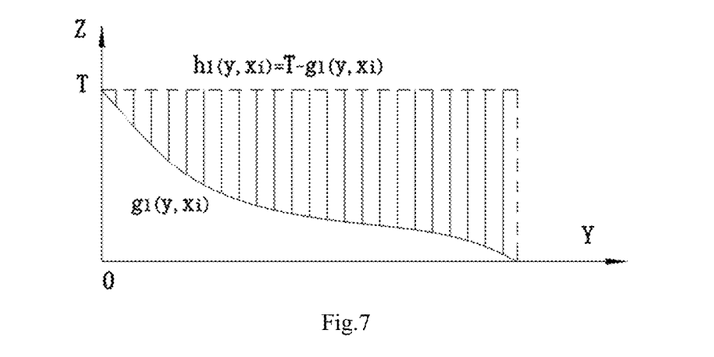
FIG. 7 is a graph showing the functional relationship between the position of the passive leaf and the magnitude of the fluence value when the front leaf in the first quadrant is used as the passive leaf according to an embodiment of the invention.

Further, step S5.2 includes the following: under the premise of a given accelerator dose rate and the blade moving in one direction, a leaf trajectory is described by a corresponding relationship between leaf position and fluence size, given the accelerator dose rate and the leaves moving along one direction;
  the leaf end position is used as the leaf position, the relationship between the leaf position and its corresponding fluence size is a monotonic function in the absence of other leaves blocking. In this embodiment, given the accelerator dose rate and the leaves moving in one direction, since the fluence value is proportional to the time, a leaf trajectory is described by a corresponding relationship between leaf position and fluence size, given the accelerator dose rate and the leaves moving along one direction. Taking the leaf end position as the leaf position, it can be found that in the absence of other blades blocking, the relationship between the leaf position and its corresponding fluence size is always a monotonic function. As shown in FIG. 6, taking any right leaves of the first quadrant as an example, the relationship between its position and its corresponding fluence is shown in the figure, denoted as g2 (x, yi), where x is the corresponding end position of the right leaves at a certain time, and yi is the corresponding ordinate of the right leaves under the coordinate system S. Similarly, the relationship between the passive leaf position and its corresponding fluence size is also a monotonic function. As shown in FIG. 7, taking the front leaves in the first quadrant as an example, when the front leaves is used as passive leaf, the front leaves retreat from the initial position 0 to the positive direction of the Y axis under the coordinate system S, and the independent shielding amount of the front blade at each position is h1 (xi,y)=T−g1(xi,y), where T is the total exposure, g1(xi,y) is the fluence corresponding to the position of the front leaves, y is the end face position corresponding to the front leaves at a certain time, and xi is the abscissa corresponding to the front leaves under the coordinate system S.

Further, step S5.3 includes the following: knowing the starting position of each leaf position, the fluence function of the next moment by the fluence function of the previous position.

Figure 8:
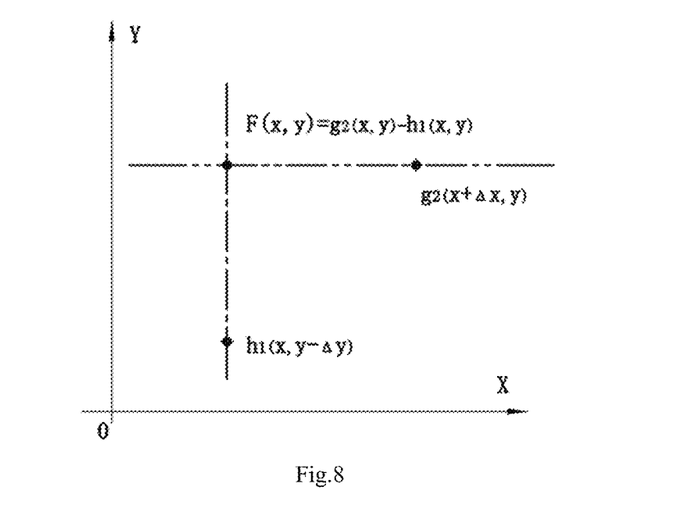
FIG. 8 is a schematic diagram of the leaf trajectory function provided by the inventive embodiment.

As shown in FIG. 8, taking the right leaves (active leaf) at any point in the first quadrant as an example, the time-lag differential equation is established for the fluence function $g_2(x, y)$ Solution, is as follows:

$$\begin{cases} g_2(x,y) = \max(g_{21}, g_{22}, g_{23}) \\ g_{21}(x,y) = g_2(x+\Delta x, y) + k_{min} \cdot \Delta x \\ g_{22}(x,y) = g_2(x+\Delta x, y) - \frac{\partial F}{\partial x} \cdot \Delta x \\ g_{23}(x,y) = g_2(x, y-\Delta y) + \frac{\partial F}{\partial y} \cdot \Delta y + k_{min} \cdot \Delta y \end{cases}$$

Specifically, $\Delta x$ and $\Delta y$ are the amount of change of the leaf position at two adjacent moments under the coordinate system S, $\partial F/\partial x$ and $\partial F/\partial y$ are the partial derivative of the fluence along x and y, and $k_{min}$ is the maximum speed limit of leaf corresponding to the minimum fluence incremental efficiency, $g_{21}(x,y)$, $g_{22}(x,y)$ and $g_{23}(x,y)$ are the fluence function values obtained by searching along the x-axis direction, the derivative along the flux surface direction, and the y-axis direction, respectively.

The above multiple embodiments can be realized in cross-over and parallel ways.

The present invention completes the dynamic segmentation of any shape target area (concave target area, annular target area, etc.) and multiple target areas through the mutual cooperative movement of the upper and lower layers of orthogonal leaves, realizes the dynamic segmentation of the upper and lower layers of the orthogonal dual-layer collimator from two directions, avoids the end surface perspective between the leaves, and improves the segmentation efficiency.

To illustrate the specific embodiment process of the present invention, an annular target area of a multi-connected region is described.

Figure 1:
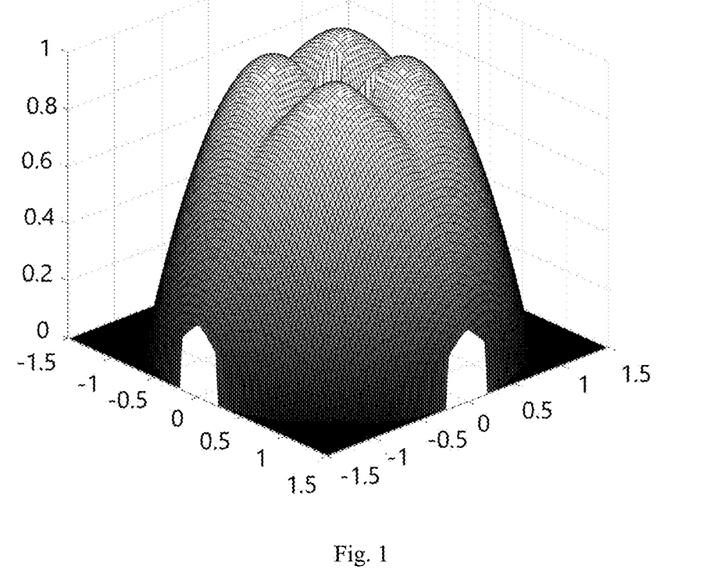
FIG. 1 shows a three-dimensional view of the strong ray fluence of a concave target region provided by the invention embodiment.
Figure 2A:
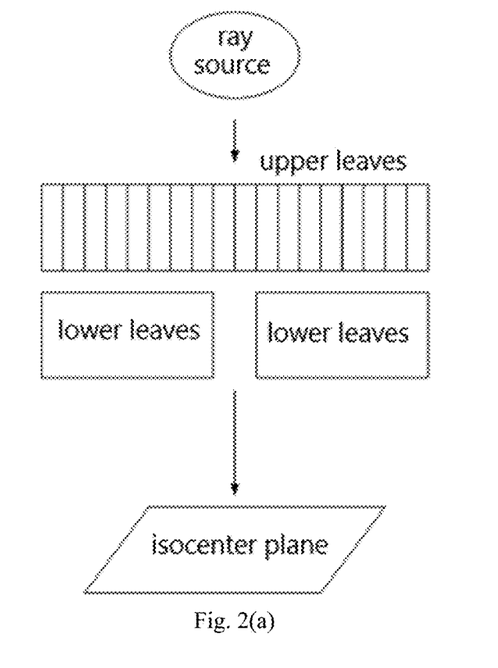
Figure 2B:
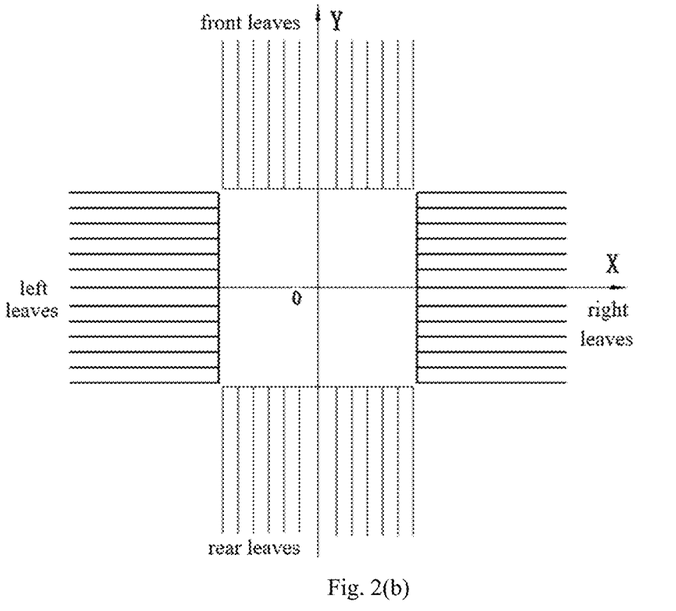
Figure 11:
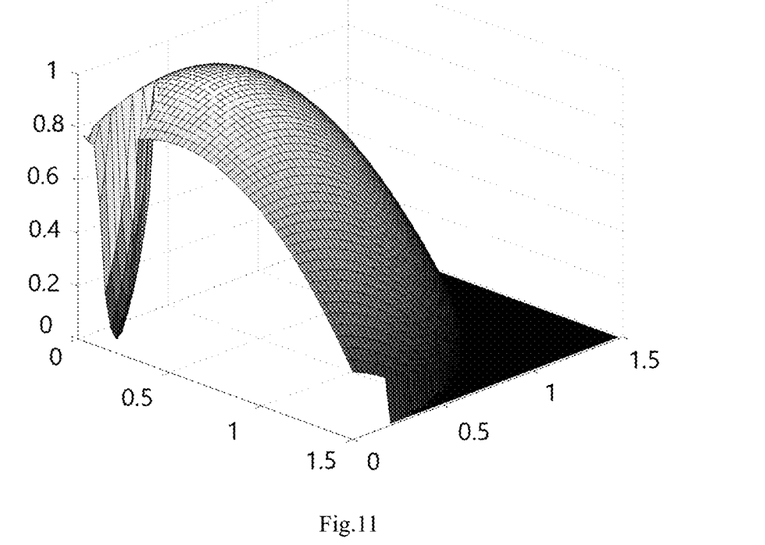
FIG. 11 is a 3D view of the fluence distribution in the first quadrant provided by the invention embodiment.
Figure 12:
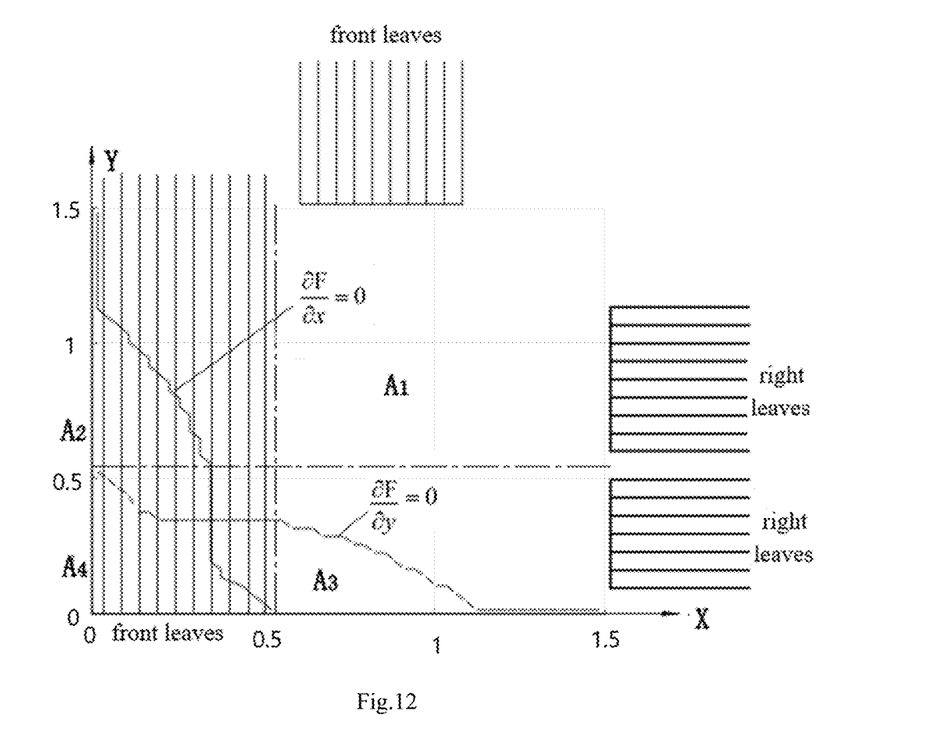
FIG. 12 is a schematic diagram of the initial position in the first quadrant after the region division provided by the invention embodiment.

The specific process is as follows:

S1: the radiation fluence of a circular target area with a multiconnected area imported from the treatment planning system can be expressed as a fluence F (x, y) within the isocenter plane, as shown in FIG. 1;

S2: use orthogonal dual-layer collimator for fluence segmentation, as shown in FIG. 2(*a*), ray through the projection of the upper and lower two collimators in the isocenter plane coordinate system S-XY, and the upper and lower leaves are located at four directions of the isocenter plane respectively, as shown in FIG. 2(*b*), the upper leaves are located at the front and rear ends of the isocenter plane, the lower leaves are located at the left and right ends of the isocenter plane;

S3: divide the quadrant to obtain the fluence distribution of the four quadrants and the corresponding leaf sequence. FIG. 11 is the fluence distribution of the first quadrant;

S4: perform regional planning of the fluence in each quadrant, obtain all regions A1, A2, A3, A4, and determine the same time. As shown in FIG. 10, taking the first quadrant as an example, the region A1 in the first quadrant is independently divided by the right leaves, the region A3 in the first quadrant is independently divided by the right leaves; the region A2 in the first quadrant is independently divided by the front leaves. And the region A4 in the first quadrant is divided by orthogonal mating of all right leaves and front leaves S5.1: after the regions are divided, determine the initial position of the active leaf and the passive leaf. In FIG. 12, the initial position of all the leaves in the first quadrant is shown. In the overlapping region A4, the front leaves in the region A4 is set as the passive leaf, and the initial positions of all the passive leaf in the region A4 are located at the junction of the quadrants, and the retraction motion is performed.

Figure 13A:
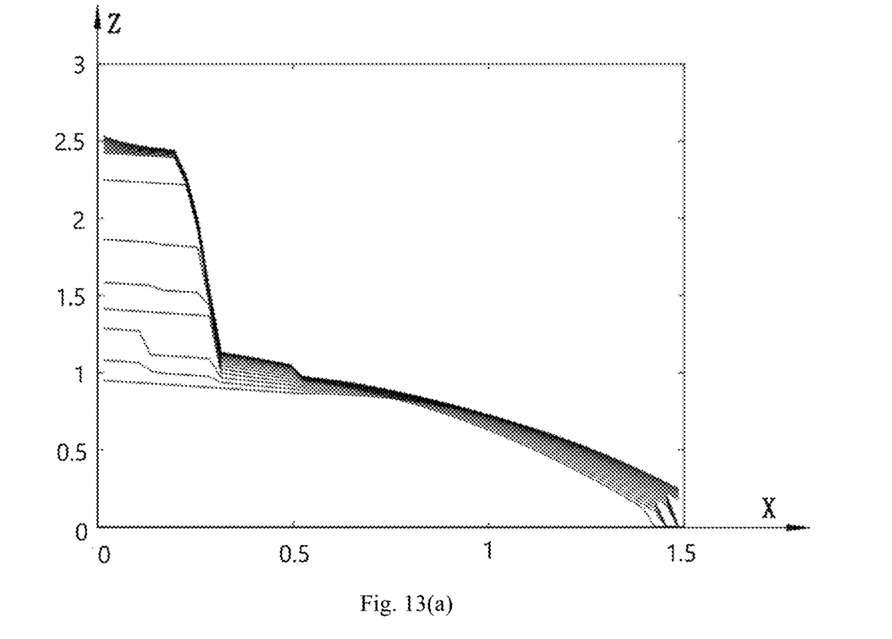
Figure 13B:
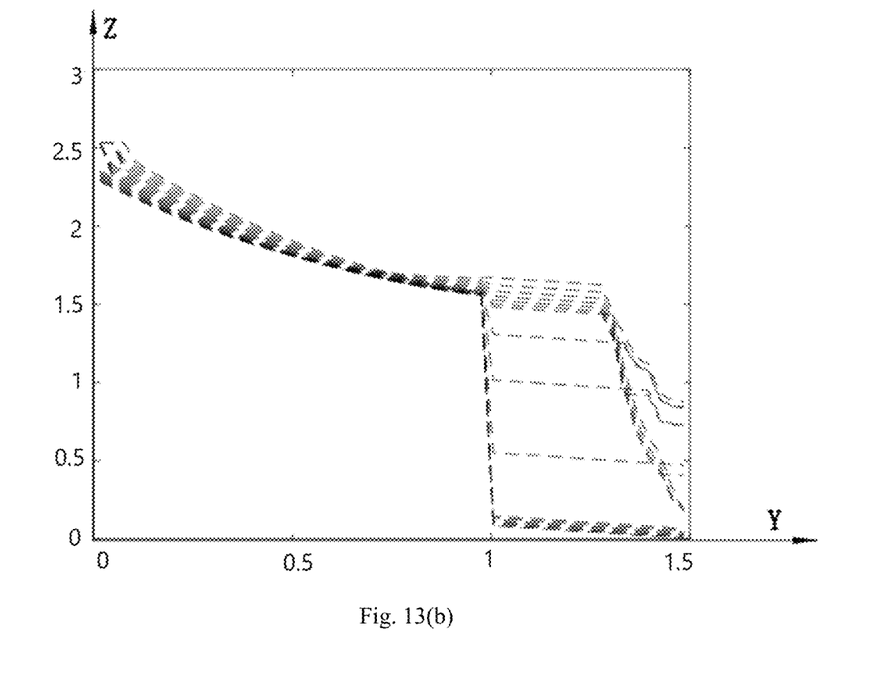

S5.2: establish the leaf trajectory function, as shown in FIG. 13, the trajectory of two groups of orthogonal leaves in the first quadrant overlapping area. FIG. 13(*a*) shows the movement of the right leaves and FIG. 13(*b*) shows the movement of the front leaves.

Figure 14:
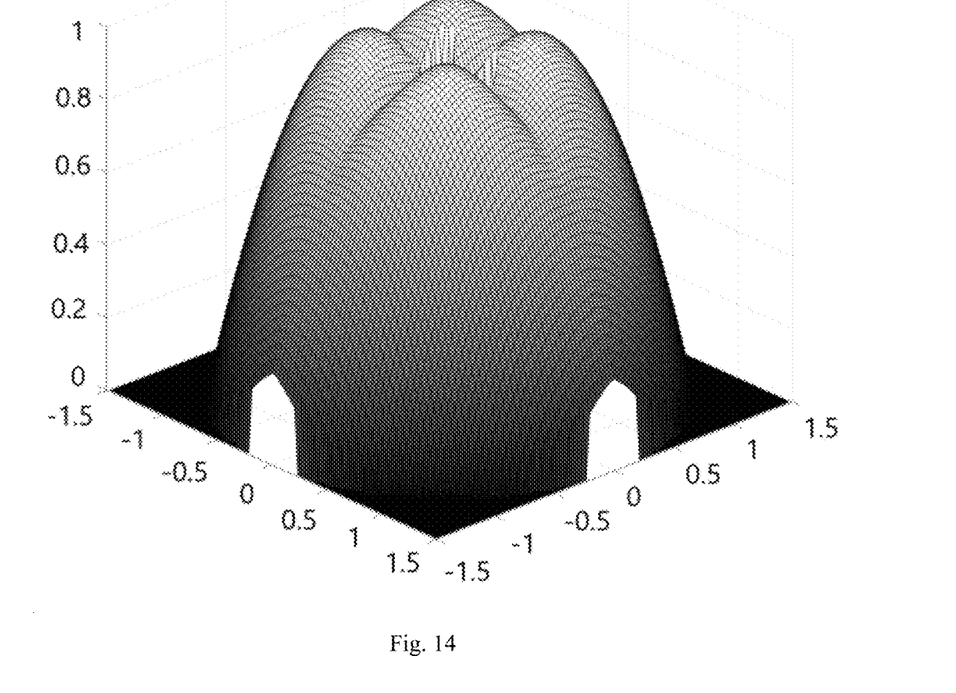
FIG. 14 is a fluence three-dimensional view segmented by the leaves trajectory provided by the invention embodiment.

S5.3: the segmented fluence F'(x, y) is calculated by the leaf trajectory without considering the influence of penumbra, and its 3D distribution is shown in FIG. 14. The relative errors are compared using the vector two norm and the initial fluence diagram as follows:

| segNum | 50 | 100 | 250 | 500 | 1000 | 10000 |
|---|---|---|---|---|---|---|
| $\Sigma\|\|F'-F\|\|_2/\Sigma F$ | 0.0416 | 0.0206 | 0.0084 | 0.0042 | 0.0021 | 2.05E−04 |

Wherein, segNum refers to the equal fraction of the fluence segmentation, which is inversely proportional to the segmentation step. The larger segNum is, the finer the segmentation of the fluence is.

The beneficial achievements of the present invention compared to the prior art are:

1. improve conformal degree: it can realize the dynamic segmentation of various complex target areas, such as concave target area and annular target area;
2. improve the segmentation accuracy: the orthogonal leaf pairs are used to cooperate with the movement, through the spatial interleaving, to avoid the leaves closed position collision, to solve the problem of the end surface perspective between the lesf pairs;
3. realize the intensity segmentation of multi-target areas: four groups of leaves with different directions can be divided into at least two, up to four quadrants, and the multi-target area problems within four can be divided simultaneously;
4. Segmentation efficiency is high: through the direction derivative characteristics of the intensity distribution surface, a peak or trough area is divided into four parts, and different leaf segmentation methods are adopted to improve the segmentation efficiency;
5. It can track the dynamic target area from two directions: a pair of orthogonal leaves is used to segment the target area, and the dynamic target area can be tracked by moving in two directions.

For the preferred embodiment of the invention, it should be noted that for ordinary persons skilled in the art, several deformation and improvements may be made without departing from the creative idea of the invention, which fall within the protection scope of the invention.

The invention claimed is:

1. An orthogonal dual-layer grating dynamic intensity modulation segmentation method based on a quadrant including the following steps:
    S1: calculating a fluence distribution under each radiation field by a treatment planning system, the fluence distribution can be expressed as a fluence F(x,y) within a radiation field range in an isocenter plane;
    S2: using an orthogonal double-layer collimator for a fluence segmentation;
    S3: dividing the quadrant, and dividing each radiation field surrounded by an upper leaf, a lower leaf, a left leaf, and a right leaf into at least two quadrants, to obtain the fluence distribution and a corresponding leaf sequence of each quadrant;
    S4: performing regional planning of the fluence F(x,y) in each quadrant to obtain multiple different regions, and determining a segmentation mode of different regions; and
    S5: for any quadrant, using two mutually orthogonal leaf groups for the fluence segmentation.

2. The orthogonal dual-layer grating dynamic intensity modulation segmentation method according to claim 1, wherein the step S2 includes projecting rays under a coordinate system S-XY of the isocenter plane, and the upper leaf and the lower leaf are located at four directions of the isocenter plane respectively.

3. The orthogonal dual-layer grating dynamic intensity modulation segmentation method according to claim 2, wherein, for the step S3, the maximum point or the minimum point in a target area can be a segmentation center.

4. The orthogonal dual-layer grating dynamic intensity modulation segmentation method according to claim 2, wherein for the step S3, if there is a concave fluence distribution or an annular target area fluence distribution, a quadrant division takes the minimum point as a segmentation center;

if there are multiple concave areas, a center of a concave target area is located on an intersection line of two quadrants.

5. The orthogonal dual-layer grating dynamic intensity modulation segmentation method according to claim 2, wherein for the step S3, after completing a quadrant segmentation, each quadrant corresponds to a ray fluence within one region of a beam range, and corresponds to at least one pair of mutually orthogonal leaf groups.

6. The orthogonal dual-layer grating dynamic intensity modulation segmentation method according to claim 1, wherein the step S4 comprises the following: surroundings of any peak or any trough in the fluence $F(x,y)$ can be divided into four regions A1, A2, A3, and A4 according to values of partial derivatives;

when $\partial F/\partial x \leq 0$, and $\partial F/\partial y \leq 0$, the region is region A1;
when $\partial F/\partial x > 0$, and $\partial F/\partial y \leq 0$, the region is region A2;
when $\partial F/\partial x \leq 0$, and $\partial F/\partial y > 0$, the region is region A3;
when $\partial F/\partial x > 0$, and $\partial F/\partial y > 0$, the region is region A4.

7. The orthogonal dual-layer grating dynamic intensity modulation segmentation method according to claim 1, wherein the step S5 comprises the following steps:

S5.1: determining an initial position of the upper leaf, the lower leaf, the left leaf, and the right leaf;

S5.2: establishing a leaf motion trajectory function; and
S5.3: applying a time-delay differential equation to solve the leaf motion trajectory function.

8. The orthogonal dual-layer grating dynamic intensity modulation segmentation method according to claim 7, wherein the step S5.1 comprises the following:

defining two orthogonal leaf groups, one group as an active leaf, the other group as a passive leaf, the active leaf moving from a beam edge to a beam center, and the passive leaf retreating from the beam center to the beam edge;

the initial position can be determined as the active leaf at the beam edge of each radiation field and the passive leaf at a quadrant junction.

9. The orthogonal dual-layer grating dynamic intensity modulation segmentation method according to claim 8, wherein the step S5.2 comprises the following:

under a premise of a given dose rate of an accelerator and a blade moving in one direction, a leaf trajectory is described by a corresponding relationship between a leaf position and a fluence size, given the dose rate of the accelerator and the upper leaf, the lower leaf, the left leaf, and the right leaf moving along the one direction;

an end position of a leaf is used as the leaf position, the relationship between the leaf position and its corresponding fluence size is a monotonic function in an absence of other leaves blocking.

10. The orthogonal dual-layer grating dynamic intensity modulation segmentation method according to claim 9, wherein the step S5.3 comprises the following:

knowing a starting position of each leaf position, the fluence $F(x,y)$ of a next moment by the fluence $F(x,y)$ of a previous position.

* * * * *